(12) United States Patent
Dillon et al.

(10) Patent No.: US 7,889,879 B2
(45) Date of Patent: Feb. 15, 2011

(54) PROGRAMMABLE AUDITORY PROSTHESIS WITH TRAINABLE AUTOMATIC ADAPTATION TO ACOUSTIC CONDITIONS

(75) Inventors: Harvey Dillon, Chatswood (AU); Justin Andrew Zakis, Beaumaris (AU); Hugh Joseph McDermott, Mount Macedon (AU); Gitte Keidser, Abbotsford (AU)

(73) Assignee: Cochlear Limited, Lane Cove (AU)

( * ) Notice: Subject to any disclaimer, the term of this patent is extended or adjusted under 35 U.S.C. 154(b) by 1116 days.

(21) Appl. No.: 10/993,359

(22) Filed: Nov. 22, 2004

(65) Prior Publication Data

US 2005/0129262 A1    Jun. 16, 2005

Related U.S. Application Data

(63) Continuation-in-part of application No. PCT/AU03/00613, filed on May 21, 2003.

(30) Foreign Application Priority Data

May 21, 2002    (AU) ...................... PS2470

(51) Int. Cl.
H04R 25/00    (2006.01)
A61N 1/00    (2006.01)

(52) U.S. Cl. .................. 381/314; 381/315; 381/326; 607/57

(58) Field of Classification Search ............... 381/314, 381/315, 320, 321, 326; 600/25; 607/55–57
See application file for complete search history.

(56) References Cited

U.S. PATENT DOCUMENTS

| | | | |
|---|---|---|---|
| 4,901,353 A * | 2/1990 | Widin ..................... | 381/312 |
| 4,953,112 A | 8/1990 | Widin et al. | |
| 5,202,927 A | 4/1993 | Topholm | |
| 5,604,812 A | 2/1997 | Meyer | |

(Continued)

FOREIGN PATENT DOCUMENTS

EP    0064042    11/1982

(Continued)

OTHER PUBLICATIONS

Supplementary European Search Report for EP 03720029 dated Nov. 12, 2008.

(Continued)

Primary Examiner—Curtis Kuntz
Assistant Examiner—Jesse A Elbin
(74) Attorney, Agent, or Firm—Kilpatrick Stockton LLP

(57) ABSTRACT

An auditory prosthesis (30) comprising a microphone (27) for receiving the sound and producing a microphone signal responding to the received sound, an output device for providing audio signals in a form receivable by a user of the prosthesis (30), a sound processing unit (33) operable to receive the microphone signal and carry out a processing operation on the microphone signal to produce an output signal in a form suitable to operate the output device, wherein the sound processing unit (33) is operable in a first mode in which the processing operation comprises at least one variable processing factor which is adjustable by a user to a setting which causes the output signal of the sound processing unit (33) to be adjusted according to the preference of the user for the characteristics of the current acoustic environment.

46 Claims, 6 Drawing Sheets

U.S. PATENT DOCUMENTS

| | | | |
|---|---|---|---|
| 5,706,351 | A | 1/1998 | Weinfurtner |
| 5,754,661 | A | 5/1998 | Weinfurtner |
| 5,852,668 | A | 12/1998 | Ishige et al. |
| 6,035,050 | A | 3/2000 | Weinfurtner et al. |
| 6,044,163 | A * | 3/2000 | Weinfurtner ................. 381/312 |
| 6,674,867 | B2 * | 1/2004 | Basseas ...................... 381/314 |
| 2002/0021814 | A1 | 2/2002 | Roeck |
| 2002/0037087 | A1 | 3/2002 | Allegro et al. |

FOREIGN PATENT DOCUMENTS

| | | |
|---|---|---|
| EP | 0712263 | 5/1996 |
| EP | 0883325 A2 | 12/1998 |
| JP | 02-020200 | 1/1990 |
| JP | 9-182194 | 7/1997 |
| WO | 2001/013364 | 2/2001 |
| WO | 0176321 | 10/2001 |
| WO | 0205591 | 1/2002 |
| WO | 0232208 | 4/2002 |

OTHER PUBLICATIONS

English translation of Japanese Office Action for 506316/2004 dated Apr. 22, 2008.

Australian Intellectual Property Office, "Examiner's First Report," issued in connection with Australian Patent Application No. 2004240216, on Apr. 11, 2007 (2 pages).

English Translation of Japanese Letter of Interrogation for JP Application No. 2004-506316, Appeal No. 2009-003961, dated Jun. 8, 2010. (3 pages).

* cited by examiner

PROGRAMMABLE AUDITORY PROSTHESIS WITH TRAINABLE AUTOMATIC ADAPTATION TO ACOUSTIC CONDITIONS

This application is a continuation-in-part of PCT/AU03/00613, entitled "Programmable Auditory Prosthesis with Trainable Automatic Adaptation to Acoustic Conditions," filed May. 21, 2003. The entire disclosure and contents of the above application is hereby incorporated by reference.

BACKGROUND

1. Field of the Invention

The present invention relates to a programmable auditory prosthesis, such as a hearing aid or cochlear implant. In particular, the invention is an auditory prosthesis that adjusts its sound processing characteristics in a particular acoustic environment in a manner that is similar or identical to that previously determined by the user of the prosthesis as optimal for that environment.

2. Related Art

Hearing loss, which may be due to many different causes, is generally of two types, conductive and sensorineural. Of these types, conductive hearing loss occurs where the normal mechanical pathways for sound to reach the hair cells in the cochlea are impeded, for example, by damage to the ossicles. Conductive hearing loss may often be helped by use of conventional hearing aid systems, which comprise a microphone, an amplifier and a receiver (miniature speaker) for amplifying detected sounds so that acoustic information does reach the cochlea and the hair cells. Since the elevation of the minimum detectable sound pressure level may vary with the frequency of an acoustic test stimulus, the amplifier may be preceded by, or comprise of, a bank of filters to enable different frequency components of the signal to be amplified by different amounts.

Sensorineural hearing loss occurs where the hair cells in the cochlea and the attached auditory nerve fibres are damaged or destroyed. Sensorineural hearing loss results in an increase in the minimum detectable sound pressure level, which often varies with the frequency of the test stimulus. However, in contrast to conductive hearing loss, the sound pressure level that is uncomfortably loud at a given test frequency is often approximately the same as for people with normal hearing. The result is a reduction in the dynamic range of sound pressure levels that are audible yet not uncomfortably loud with the impaired ear, and this dynamic range of the impaired ear may vary considerably with the frequency of the acoustic test stimulus. For this reason, sensorineural hearing loss is often treated with hearing aid systems that employ non-linear amplification to compress the dynamic range of common sounds towards the dynamic range of the impaired ear. Such systems may use a filter bank that is followed by a bank of compressive amplifiers, so that the dynamic range of the signal is reduced by an amount that is considered appropriate for the dynamic range of the impaired ear in each band.

In many people who are profoundly deaf, the reason for deafness is absence of, or destruction of, the hair cells in the cochlea which transduce acoustic signals into nerve impulses. These people are thus unable to derive suitable benefit from hearing aid systems, no matter how much the acoustic stimulus is amplified, because there is damage to or absence of the mechanism for nerve impulses to be generated from sound in the normal manner. It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Cochlear implant systems have typically consisted of two essential components, an external component commonly referred to as a processor unit and an internal implanted component commonly referred to as a stimulator/receiver unit. Traditionally, both of these components have cooperated together to provide the sound sensation to a user.

The external component has traditionally consisted of a microphone for detecting sounds, such as speech and environmental sounds, a speech processor that converts the detected sounds, particularly speech, into a coded signal, a power source such as a battery, and an external transmitter coil.

The coded signal output by the speech processor is transmitted transcutaneously to the implanted stimulator/receiver unit situated within a recess of the temporal bone of the user. This transcutaneous transmission occurs via the external transmitter coil which is positioned to communicate with an implanted receiver coil provided with the stimulator/receiver unit. This communication serves two essential purposes, firstly to transcutaneously transmit the coded sound signal and secondly to provide power to the implanted stimulator/receiver unit. Conventionally, this link has been in the form of an RF link, but other such links have been proposed and implemented with varying degrees of success.

The implanted stimulator/receiver unit traditionally includes a receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

Different users of auditory prostheses require differing outputs from their prosthesis to suit their individual requirements. This is the case even when individual users may clinically be regarded as having identical hearing loss profiles, are utilising identical prostheses, and when exposed to essentially identical acoustic environments. Because of this, sound processing schemes for hearing aids and cochlear implants typically contain a number of parameters for which the values can be adjusted to suit the requirements of individual users. Examples of such parameters include the sensitivity to incoming sounds and the variation of the frequency response. Typically, the parameter values are selected either by the prosthesis user in everyday situations (eg. the sensitivity (volume), frequency response), or by the clinician at the time the prosthesis is fitted (eg. the baseline frequency response and the rate at which the frequency response and sensitivity vary as the input level varies).

In more recent times, there has been a trend to provide auditory prostheses with an increasing number of adjustable parameters that can or must be adjusted to optimise performance. This increase has, however, highlighted the problem that there does not always exist a reliable prescriptive method for selecting the optimum values for the individual user, particularly as some optimum values may vary among individuals who have hearing loss profiles that may clinically be regarded as identical. It is accordingly often necessary for the clinician to make adjustments to the prosthesis based on the user's reported experiences away from the clinic, and the need to return to the clinic for these adjustments can be time consuming and inefficient.

One example of a hearing aid that can receive the impressions of a hearing aid user and take these into consideration during operation is described in U.S. Pat. No. 5,604,812. This document describes a hearing aid that has a memory that can store so-called "unsharp inputs", or impressions of the hearing aid wearer about prevailing ambient conditions and/or the volume of the output of the hearing aid, prescribable algorithms, hearing loss data and hearing aid characteristic data. A fuzzy logic module uses this data and control signals from an input signal analysis unit to calculate the output setting parameters for the hearing aid. The behaviour rules of the fuzzy logic module and/or the prescribable algorithms are calculated from the data stored in the aid's memory by a neural network, with the neural network being typically implemented on a personal computer that is connected to the aid. A problem with such an aid is the complexity of the processing scheme and an undesirably large drain on the aid's power source, typically an on-board battery. Further to this, such an aid would require a large amount of clinical time to correctly "train", as the user does not have direct control over what is optimal, and "unsharp inputs" are used in the training of the aid rather than precise and direct inputs.

Another example of a hearing aid that can receive the preferences of a hearing aid user and take these into consideration is described in U.S. Pat. No. 6,035,050. Such an aid requires the user to identify their current listening environment by selecting one of a limited number of listening situations on a remote unit. Should the user find that their current listening situation does not readily fall within those provided for selection, the benefit of such a aid becomes greatly reduced. Further to this, some listening situations on the remote unit, such as "at work", may consist of a range of different acoustic environments and hence may not be acoustically well-defined. Thus, a neural network may not be able to reliably recognise such listening situations from an analysis of the microphone signal that, due to practical considerations such as memory limitations and the desirability of fast recognition of a change in listening situation, must be limited to a period of seconds or a few minutes. Therefore, after training it is possible that the neural network may misclassify a listening situation, especially in situations that are not acoustically well-defined, which can result in the application of amplification parameters that are unsuitable for the current listening situation. In such a device focus is placed on attempting to categorise specific acoustic environments, rather than measure the parameters of the environment and use these parameters directly in the processing scheme, as is the case with the present invention. Another disadvantage of this device is that a major lifestyle change, such as a new workplace that is acoustically different to the previous workplace, may require different amplification parameters and hence a return visit to the clinic.

Another example of a hearing aid that can receive the preferences of a hearing aid user and take these into consideration is described in U.S. Pat. No. 6,044,163. This document describes a hearing aid that is similar to the hearing aid described in U.S. Pat. 6,035,050. A major difference is that the neural network is not restricted to selection of sets of amplification parameters that are stored in a memory, but may directly set the value of individual amplification parameters. The disadvantages of the hearing aid described in this patent are similar to those of the hearing aid described in U.S. Pat. No. 6,035,050.

The present invention is adapted to providing users with an auditory prosthesis that is adaptable and can adjust its output to the user when that user is exposed to varying ambient acoustic environments.

Further, the present invention is adapted to providing users with an auditory prosthesis that can be 'trained' by the individual user to adapt its output to the user's preference in listening conditions encountered away from a traditional clinical situation, thereby reducing the clinical time required to fit an optimise a prosthesis to the individual user.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY

According to a first aspect, there is disclosed an auditory prosthesis comprising:

a microphone for receiving sound and producing a microphone signal corresponding to the received sound;

an output device for providing audio signals in a form receivable by a user of the prosthesis;

sound processing means operable to receive the microphone signal and carry out processing operations on the microphone signal to produce an output signal in a form suitable to operate the output device, and user control means;

wherein the processing means is operable in a first mode in which the processing operation comprises at least one variable processing factor which is adjustable by a user using the user control means to a corresponding setting which causes the output signal of the sound processing means to be adjusted according to the preference of the user in the current acoustic environment; and wherein the sound processing means is simultaneously operable in a second mode in which at least one of the at least one variable processing factor(s) is automatically adjusted on the basis of one or more previously selected settings.

Preferably, the control means can be adjusted throughout a substantially continuous range of settings, with the preferred setting being used to calculate the one or more variable processing factors, which alter the processing operations applied to the microphone signal.

Preferably, the settings of the control means are related to one or more variable processing factors by defined mathematical relationships incorporating coefficients, and where the values of said coefficients are calculated to be those values that cause the variable processing factors to best approximate the variable processing factors that occurred as a result of previous settings of the control means.

In this invention, it will be appreciated that what is considered an optimal output signal by one user may not be considered an optimal signal by another user. The present invention ensures that the prosthesis operates in a manner that suits the requirements of the user for the acoustic environments that the user encounters rather than in some manner predetermined from clinical tests which may not replicate the type of acoustic environments to which the user is routinely or occasionally exposed, and which may not necessarily replicate the subjective reactions of users when in those environments.

Preferably, the data memory means stores data sets representative of the characteristics of at least one acoustic environment. Preferably the at least one variable processing factor is automatically adjusted on the basis of the acoustic environments in which at least one variable processing factor was selected.

In a first embodiment, the processing means may be adapted when operable in the first mode to offer two or more possible optimal settings of the variable processing factor for selection by the user. In this case, the user is preferably able to compare the operation of the prosthesis when operating in a particular acoustic environment when operating with each setting and then select from these the setting that is best for that particular environment. The setting of the variable processing factor that is selected by the user may then be stored in the data memory means, optionally with data indicative of the characteristics of the particular acoustic environment. This process may be repeatable so as to allow the processing means to monitor whether the user's preference for a particular setting of the variable processing factor changes with time or usage. In this way, the user effectively selects or votes for the best setting each time. By repeating the process, the number of selections or votes made by the user for each setting may be monitored to allow the prosthesis to select the optimal setting of the variable processing factor or optionally, the optimal setting of the variable processing factor for a particular environment.

In this embodiment, the user may alternate between listening with the offered settings by operating a control means, and can select or vote for a setting of the variable processing factor(s) by operating an indicator means. In one embodiment, the control means may comprise a switch or set of buttons that is actuable by the user, and the indicator means may comprise a switch or button that is actuable by the user.

In another embodiment, the processing operation of the processing means may be adjustable by the user when the processing means is in the first mode of operation. Rather than offering a discrete selection of possible optimal settings for selection by the user, in this embodiment, the user is able to adjust a control means throughout a substantially continuous range that allows the user to alter the variable processing factor(s) throughout a range of values, and thus alter the processing operation of the processing means. Once the user has adjusted the control means to a setting in the substantially continuous range that is considered by the user an optimal setting for a particular acoustic environment, the user may operate an indicator means, such as a switch or button, leading to storage of that setting and optionally, data indicative of the particular acoustic environment in the data memory means. Actuation of this indicator means may be taken by the processing means as indicating that the particular setting of the control means at that time is considered optimal by the user for the particular acoustic environment in which the user finds themself.

In this embodiment, the control means may comprise a rotary wheel control. The rotary wheel control may be mounted on the housing of the prosthesis or alternatively, may be mounted on a remote unit. The control means could also be in the form of a toggle switch or press buttons.

In the above embodiments, the indicator means may be mounted on a housing of the prosthesis. In another embodiment, the indicator means may be mounted on a remote unit.

In a preferred embodiment, the settings selected by the user as being optimal to that user for a plurality of acoustic environments may be stored in the data memory means and optionally, with data indicative of the characteristics of those particular acoustic environments. The processing means operates in the second mode, and may simultaneously be operable in the first mode for a defined period of time or can be considered as operating in the first mode every time the user adjusts the control means and selects what is considered a new optimal setting for that particular environment. In another embodiment, the prosthesis may have a defined training period in which the prosthesis may be operable in the first mode of operation. This period may be as long as the user wishes or optionally, the prosthesis may signal to the user when the training period is complete. In this case, the prosthesis may be adapted to indicate the training period is complete once there has been a particular pre-defined number of instances in which the user has not selected a setting which is substantially different to the setting already estimated by the prosthesis to be optimal.

In a preferred embodiment, the prosthesis may further comprise a sound analysis means. The sound analysis means preferably receives input signals from the microphone and monitors the acoustic environment of the prosthesis user. The sound analysis means preferably provides an output representative of the acoustic environment being monitored at that time.

In a further embodiment, the data memory means may comprise one or more data memory locations. In one embodiment, the data memory means may comprise five data memory locations. In this embodiment, the first data memory location may contain the audiometric data of the prosthesis user and/or individual data for one or more loudness models used by the prosthesis. The second data memory location may contain characteristic data about the hearing prosthesis. The third data memory location may comprise one or more equations used to predict the optimal processing operation of the processing means for an individual user in different acoustic environments. The fourth data memory location may store the optimal sound processing data as selected by the user of the prosthesis. This data may be ordered in different ways, such as sequentially or indexed according to the corresponding acoustic environment data supplied by the sound analysis means. The acoustic environment data that corresponds to the optimal sound processing data is optionally stored in the fifth data memory location. Other data memory means having differing numbers of memory locations may be envisaged.

In one embodiment, the fourth data memory location may store a predefined maximum number of sets of optimal sound processing data. In one embodiment, the memory location may store a maximum of 400 data sets. Other maximum numbers can, however, be envisaged. In one embodiment, the data processing means does not utilise all stored data sets but only a predefined number of most recently logged data sets. For example, the data processing means may only utilise the last 256 data sets when determining the optimal value of a variable processing factor. In one embodiment, the newest data set to be stored in the memory location can be stored instead of the oldest data set in the memory location. This first in first out storage system ensures only the most recently logged data is ever stored in the prosthesis at any one time. In another embodiment, older data cannot be overwritten such that once the memory location is full no further data sets can be logged by the prosthesis. In another embodiment, old data is preferably selectively overwritten by the newest sound processing data according to the acoustic environment in which the sound processing data was selected.

In a further embodiment, the prosthesis preferably further comprises a data processing means. The data processing means preferably receives the output of the sound analysis means. Based on the output of the sound analysis means, the data processing means can be adapted to calculate the loudness of sounds present at the microphone. In one embodiment, the data processing means can calculate the loudness of the sounds as they would appear to a person with normal hearing and/or to a person with a degree of hearing impairment. The data processing means can be adapted to calculate other acoustic and psychoacoustic measures of the sounds present at the microphone. The data processing means can use the acoustic and/or psychoacoustic measures as inputs to the one or more equations stored in the third data memory location which estimate the optimal sound processing operation of the sound processing means for the user in the acoustic environments represented by the sound analysis means.

The data processing means further preferably uses the hearing prosthesis characteristic data stored in the second data memory location and the optimal sound processor data generated by the equations to automatically and continuously determine the appropriate setting of the processing means to provide the optimal output signal for the user in the current acoustic environment being experienced by the user.

In a preferred embodiment, the processing means can include an amplifier means and a gain control means. In this case, the operation of the amplifier means is preferably adjustable when in the first mode to allow the user to optimise the gain at each or every frequency of the amplifier in a particular acoustic environment. Once optimised, the prosthesis operates in a second mode in which the amplification characteristics of the amplifier means automatically adjusts to the optimal level. That is, in such embodiments the variable processing factor is preferably the amplifier gain at each or every frequency.

In a preferred embodiment of the above aspects, the gain at each or every frequency of the amplifier means is calculated through use of an equation having a pre-defined form. In one form the equation can be:

$$G_i = a_i + b_i * \max(L_i, c_i) + d_i * (SNR_i - SNR_{av}) \quad (1)$$

where i=the frequency band number;
$G_i$=gain for band i;
$a_i$=trainable coefficient for band i;
$b_i$=trainable coefficient for band i;
$c_i$=trainable coefficient for band i;
$d_i$=trainable coefficient for band i;
$L_i$=sound pressure level at the microphone in band i;
$SNR_i$=signal to noise ratio in band i; and
$SNR_{av}$=average SNR in all bands.

Other forms of the equation with other acoustic or psychoacoustic parameters, such as higher-order moments of the spectrum of the signal and variations of these moments with time, or other statistical parameters or estimates of the acoustic signal or combinations of these parameters, and optionally with other additional coefficients, can calculate the gain or processing factors other than gain, such as the speed at which the prosthesis reacts to change in the acoustic environment, the choice of the equations used will depend upon the particular application desired, with such applications falling within the scope of the present invention.

In the above embodiment, trainable coefficients include a, b, c and d, which as a result leads to the amplifier gain G being a variable processing factor.

Thus, in embodiments of the invention, more than one variable processing factor of the processing means can be adjustable by the user using the control means or multiple control means. Similarly, more than one variable processing factor of the processing means can be automatically adjusted as appropriate to any acoustic environment. In this embodiment, the control means or multiple control means can allow the user to adjust one or more of the following example operations of the processor means:

(i) the volume of the output signal;
(ii) the gain of the output signal at particular frequencies relative to other frequencies, for example the mid frequency gain can be boosted or attenuated with respect to the low or high band frequencies of the output signal; and
(iii) a slope control where the low and high frequency band gains are adjusted in opposing directions while the mid band gain is unchanged.

In this embodiment, for each of the operations of the processor means the user can select a setting which is optimal for each variable processing factor for the particular acoustic environment that they are in by actuating the indicator means. On multiple operations of the control means the user may select a setting which is optimal for one or more variable processing factors for the acoustic environment that the user experiences by actuating the indicator means. Thus, more than one operation of the sound processor means, as well as more than one variable processing factor, can be adjusted in combination for each vote or selection. Each time the indicator means is actuated, the gain in each frequency band is preferably recorded along with a data set indicative of the acoustic environment detected by the microphone. This data can be used with previous sets of data by the data processing means to calculate the gain equation coefficients that best match the logged training data in each band. The recorded gain in each frequency band may be used to calculate the gain equation coefficients.

In a further embodiment, when operating in the first mode the data processing means preferably does not calculate optimal gain equation coefficients until a predetermined number of selections have been made by the user. In one embodiment, the prosthesis can be adapted to not calculate optimal gain equation coefficients until at least fifty selections have been made by the user. In this case, where the predetermined number of selections have not been made, the processing means may when operating in the second mode preferably automatically calculate the output appropriate to the current environment, based on predetermined coefficients and/or variable processing factors. Once the predetermined number of selections have been made, the processing means may calculate the optimal gain equation coefficients on the basis of previous user preferences when in the first mode of operation, and automatically and continuously calculate the variable processing factors with these equations when in the second mode of operation. In another embodiment, the data processing means preferably does not wait for a predetermined number of selections to be made by the user before calculating the optimal gain equation coefficients, but preferably does not use the calculated coefficients when in the second mode of operation until the variable processing factors that are preferred by the user can be predicted with the equations and calculated coefficients with a certain degree of accuracy.

In an alternative embodiment, equations may not be used to determine the optimal variable processing factors for different environments. The optimally adjusted variable processing factors may be stored in the fourth data memory at locations determined by the corresponding acoustic environment data supplied by the sound analysis means. Prior to the commencement of operation in the first mode, the memory locations are preferably loaded with processing factors that are derived from empirical observations or prescriptive procedures for the corresponding acoustic environment parameter values. When operating in the first mode the optimally adjusted processing factor(s) may be stored in the fourth data memory at locations determined by the acoustic environment data. The optimally adjusted processing data may simply overwrite the prescribed data, or may be combined with old data written to the same location using a mathematical and/or statistical procedure. When operating in the second mode, the data supplied by the sound analysis means may be used to index the fourth data memory location, and the value(s) stored at the indexed memory location are preferably used to set the target value(s) of the corresponding processing factor(s) for the sound processing means. The processing factor(s) applied in the sound processing means may slowly converge towards the target value(s) to avoid the possibility of undesirable acoustic effects associated with excessively rapid or instantaneous changes of the applied value(s). This alternative embodiment eliminates the need for the fifth data memory location and the equations stored in the third data memory location, and hence the variation of a processing factor with the acoustic environment is not restricted by the relationships that are predefined in the equations.

In another alternative embodiment, the optimally adjusted variable processing factor(s) may be stored in the fourth data memory location and a mathematical and/or statistical procedure is used to calculate the optimal value of the processing factor(s). This alternative embodiment eliminates the need for the equations stored in the third data memory location, and the storage of acoustic environment data either directly in the fifth data memory location or to index setting data in the fourth data memory location. This alternative embodiment is an appropriate simplification for processing factors that do not vary with the acoustic environment, such as the maximum permissible level of the output of a hearing aid or cochlear implant before the output is uncomfortably loud.

In a further embodiment, the user can train the prosthesis to provide optimal variable processing factors for different listening criteria, such as to maximise speech intelligibility, listening comfort, or pleasantness. In one embodiment, an equation similar in form to equation 1 can comprise acoustic environment or psychoacoustic parameters that are highly correlated to a particular listening criterion, such as maximising speech intelligibility or listening comfort. When operable in the second mode the variable processing factors may automatically adapt for the predicted weighted combination of listening criteria as determined by the values of the coefficients and the acoustic environment and/or psychoacoustic parameters used by the equations.

In another embodiment, while operable in the first mode the user may indicate the listening criterion or combination of criteria used to determine the preferred adjustment of the variable processing factor(s) with an indicator means, or optionally the aid automatically predicts the listening criterion or combination of criteria from the values of acoustic environment and/or psychoacoustic parameters that are known to correlate with different listening criteria, and/or from the presence of signals of interest such as speech and music as detected by the prosthesis. The fourth data memory location (otherwise referred to as a first data memory location) may be divided into sections for different listening criteria, and the optimally adjusted variable processing factor(s) may be stored in a memory location(s) as determined by the listening criterion or combination of listening criteria under which they were adjusted by the user. The fifth data memory location (otherwise referred to as a further data memory location) is optionally also divided into sections for each different listening criterion for the storage of the acoustic or psychoacoustic parameter values that correspond to the values stored in the fourth data memory location. With this structure, the data in each section of the fourth and fifth data memory locations is preferably used to calculate the optimal coefficients of variable processing factor equations similar in form to equation 1 for each listening criterion. When operable in the second mode, the user can indicate the current listening criterion or combination or criteria via an indicator means or alternatively, the listening criterion or weighted combination of criteria can be predicted from the values of acoustic environment and/or psychoacoustic parameters that are known to correlate with different listening criteria and/or the presence of signals of interest such as speech and/or music, or by one or more trainable listening criteria equations that have acoustic environment or psychoacoustic parameters as their input, where the optimal coefficients of each listening criterion equation are calculated from the data stored in the corresponding sections of the fourth and fifth data memory locations. Once the listening criterion or weighted combination of listening criteria are either indicated by the user or automatically predicted by the prosthesis, the optimal variable processing factors may be calculated with equations similar in form to equation 1 for each criterion, and are combined according to the indicated or predicted weighting of the listening criteria.

In an alternative embodiment, when operable in the first mode the listening criterion or combination of criteria indicated by the user via an indicator means or predicted by the prosthesis may be used in addition to the corresponding acoustic environment and/or psychoacoustic parameters to index the location in the fourth data memory where the optimally adjusted variable processing factor(s) are stored. When operable in the second mode, the current values of acoustic environment and/or psychoacoustic parameters and the indicated and/or predicted listening criterion or combination or criteria may be used to index the fourth data memory location to retrieve the optimal variable processing factor(s) for the prevailing conditions. In another embodiment, the listening criterion or combination of criteria may not be used to index the fourth data memory location, and the processing factor value(s) stored at each location in the fourth data memory when operable in the first mode may be modified according to the weighted combination of listening criteria for the particular acoustic environment.

In the above embodiments, the listening criterion or combination of criteria is indicated by the user by an indicator means, such as a switch, toggle switch, or set of pushbuttons on the housing of the prosthesis, or alternatively on a remote unit.

According to a second aspect, the present invention provides an auditory prosthesis comprising:

a microphone which receives sound and produces an output signal corresponding to the received sound;

an output device that provides audio signals in a form receivable by a user of the prosthesis;

a sound processing means operable to receive the microphone signal and carry out a processing operation on the microphone signal to produce an output signal in a form suitable to operate the output device, wherein the processing means is operable in a first mode in which the processing operation comprises at least one variable processing factor which is adjustable by a user to a setting which causes the output signal of the processing means to be adjusted according to the preference of the user for the characteristics of the current acoustic environment;

a sound analysis means that also receives the microphone signal and outputs a data set representative of the acoustic environment;

a data memory means for storing a plurality of said user adjusted settings; and a data processing means that analyses said stored settings and is operable to output control signals to the sound processing means;

wherein, upon receiving control signals from the data processing means, the sound processing means is simultaneously operable in a second mode in which said at least one variable processing factor is automatically adjusted on the basis of the previously adjusted variable processing factor selected by the user.

In this aspect, the features of the prosthesis can have the features as described above with reference to the first aspect where such features are compatible with the operation of the prosthesis as described therein.

In this aspect, the hearing prosthesis preferably uses the data memory means to store a record of optimal settings as determined by the user of the prosthesis for different acoustic environments. This record is then used by the data processing means to calculate coefficients of one or more equations that are used to predict the optimal setting of the processing operation of the speech processor for that user when exposed to a different acoustic environment.

In one embodiment, the hearing prosthesis can be adapted to output audio signals to a single ear of the user. In another embodiment, the hearing prosthesis can be adapted to output audio signals to both ears of the user. In yet a further embodiment, signals from the inputs of two prosthesis can be connected to the sound analysis means by wire or wirelessly. The control means for the above embodiments can be located on the housing of each prosthesis, a remote unit for each prosthesis, or the control means for both prostheses can be located on a common remote unit.

In one embodiment of the above aspects, the hearing prosthesis can be a hearing aid. In this embodiment, the output device of the hearing aid can be an earphone that receives the output signal of the processing means and generates amplified sounds that are delivered into the ear of the user.

In another embodiment, the hearing prosthesis can be an implanted hearing aid device whereby the output device of the prosthesis can be a vibrating mechanism, mechanically coupled to the middle or inner ear.

In another embodiment of the above aspects, the hearing prosthesis can be a cochlear implant. In this embodiment, the output device can comprise a receiver/stimulator unit that receives encoded stimulation data from the processing means and outputs stimulation signals that are delivered to the cochlea through an electrode array. In this embodiment, the sound processing means can comprise a speech processor that uses a coding strategy to extract speech from the sounds detected by the microphone before or after processing of the microphone signal according to the variable processing factors. In one embodiment, the speech processor of the cochlear implant can perform an audio spectral analysis of the acoustic signals and output channel amplitude levels. The transformation from the spectrum of the acoustic signal to electrical channel amplitude levels may be determined by a variable processing factor based on previously selected variable processing factors. The threshold and discomfort channel amplitude levels can also be processing factors that are based on previous adjustments and selections made by the prosthesis user. The sound processor can also sort the outputs in order of magnitude, or flag the spectral maxima as used in the SPEAK strategy developed by Cochlear Ltd.

The receiver/stimulator unit is preferably positioned within a housing that is implantable within the user. The housing for the receiver/stimulator unit is preferably implantable within a recess in the bone behind the ear posterior to the mastoid.

The speech processing means is, in use, preferably mounted external to the body of the user such that the signals are transmitted transcutaneously through the skin of the user. Signals can preferably travel from the processing means to the receiver means and vice versa. The receiver/stimulator unit can include a receiver coil adapted to receive radio frequency (RF) signals from a corresponding transmitter coil worn externally of the body. The radio frequency signals can comprise frequency modulated (FM) signals. While described as a receiver coil, the receiver coil can preferably transmit signals to the transmitter coil which receives the signals.

The transmitter coil is preferably held in position adjacent the implanted location of the receiver coil by way of respective attractive magnets mounted centrally in, or at some other position relative to, the coils.

During use, the microphone is preferably worn on the pinna of the user, however, other suitable locations can be envisaged, such as a lapel of the implantee's clothing. The speech processor preferably encodes the sound detected by the microphone into a sequence of electrical stimuli following given algorithms. The encoded sequence is transferred to the implanted receiver/stimulator unit using the transmitter and receiver coils. The implanted receiver/stimulator unit may demodulate the FM signals and allocates the electrical pulses to the appropriate attached electrode by an algorithm which is consistent with the chosen speech coding strategy.

The external component housing the processing means further preferably houses a power supply. The power supply can comprise one or more rechargeable batteries. The transmitter and receiver coils may be used to provide power via transcutaneous induction to the implanted receiver/stimulator unit and the electrode array.

While the implant system can rely on external componentry, in another embodiment, the microphone, speech processor and power supply can also be implantable. In this embodiment, the implanted components can be contained within a hermetically sealed housing or the housing used for the stimulator unit.

According to a third aspect there is provided a method of adjusting an auditory prosthesis by a user in an acoustic environment comprising the steps of:

producing a microphone signal from a microphone that corresponds to sound received by the microphone;

providing audio signals, through an output device, in a form receivable by the user;

carrying out a processing operation, through a sound processing means, on the microphone signal so as to produce an output signal in a form suitable to operate the output device wherein the processing means is operable in a first mode in which the processing operation comprises at least one variable processing factor which is adjustable by a user to a setting which causes the output signal of the sound processing means to be adjusted according to the preference of the user for the characteristics of the current acoustic environment;

storing the setting in a data memory means;

wherein the sound processing means is simultaneously operable in a second mode in which said at least one variable processing factor is automatically adjusted on the basis of the previously adjusted variable processing factor selected by the user.

According to a fourth aspect there is provided a method of adjusting an auditory prosthesis by a user in an acoustic environment comprising the steps of:

producing a microphone signal from a microphone that corresponds to sound received by the microphone;

providing audio signals, through an output device, in a form receivable by the user;

carrying out a processing operation, through a sound processing means, on the microphone signal so as to produce an output signal in a form suitable to operate the output device wherein the processing means is operable in a first mode in which the processing operation comprises at least one variable processing factor which is adjustable by a user to a setting which causes the output signal of the sound processing means to be adjusted according to the preference of the user for the characteristics of the current acoustic environment;

receiving the microphone signal at a sound analysis means that subsequently outputs a data set representative of the acoustic environment of the prosthesis;

storing a plurality of user adjusted settings in a data memory means;

analysing the stored user adjusted settings and transmitting control signals to the sound processing means;

wherein, upon receiving the control signals, the sound processing means is simultaneously operable in a second mode in which said at least one variable processing factor is automatically adjusted on the basis of the previously adjusted variable processing factor selected by the user.

The present invention enables the user of an auditory prosthesis to adjust the operation of the processing means in a simple way while they are using the prosthesis in a normal way. The invention further eventually allows the user to 'train' the prosthesis to adjust its operation automatically. This has a number of advantages including:

(1) greater levels of user satisfaction for both hearing aids and cochlear implants, because of the better control users have over their hearing;

(2) improved listening comfort, and/or speech intelligibility and/or subjective sound quality, because processing parameters are optimised by each user to the personal preference and needs of each user;

(3) the ability to generalise the 'training' algorithm to work effectively with future devices that have different, or additional, parameters that require adjustment;

(4) because the training is carried out by the user in daily life, expensive clinical time is not required to achieve adjustment of the hearing aid and as adjustment is carried out in real life conditions, the adjustment better relates to actual performance of the device, rather than ideal clinical conditions; and (5) The ability to generalise the training algorithm to work effectively in environments for which no training has been provided by the user, by automatically applying the general relationships between preferred variable processing factors and acoustic characteristics that have been established by the training.

BRIEF DESCRIPTION OF THE DRAWINGS

By way of example only, a preferred embodiment of the invention is now described with reference to the accompanying drawings, in which.

DETAILED DESCRIPTION

Figure 1:
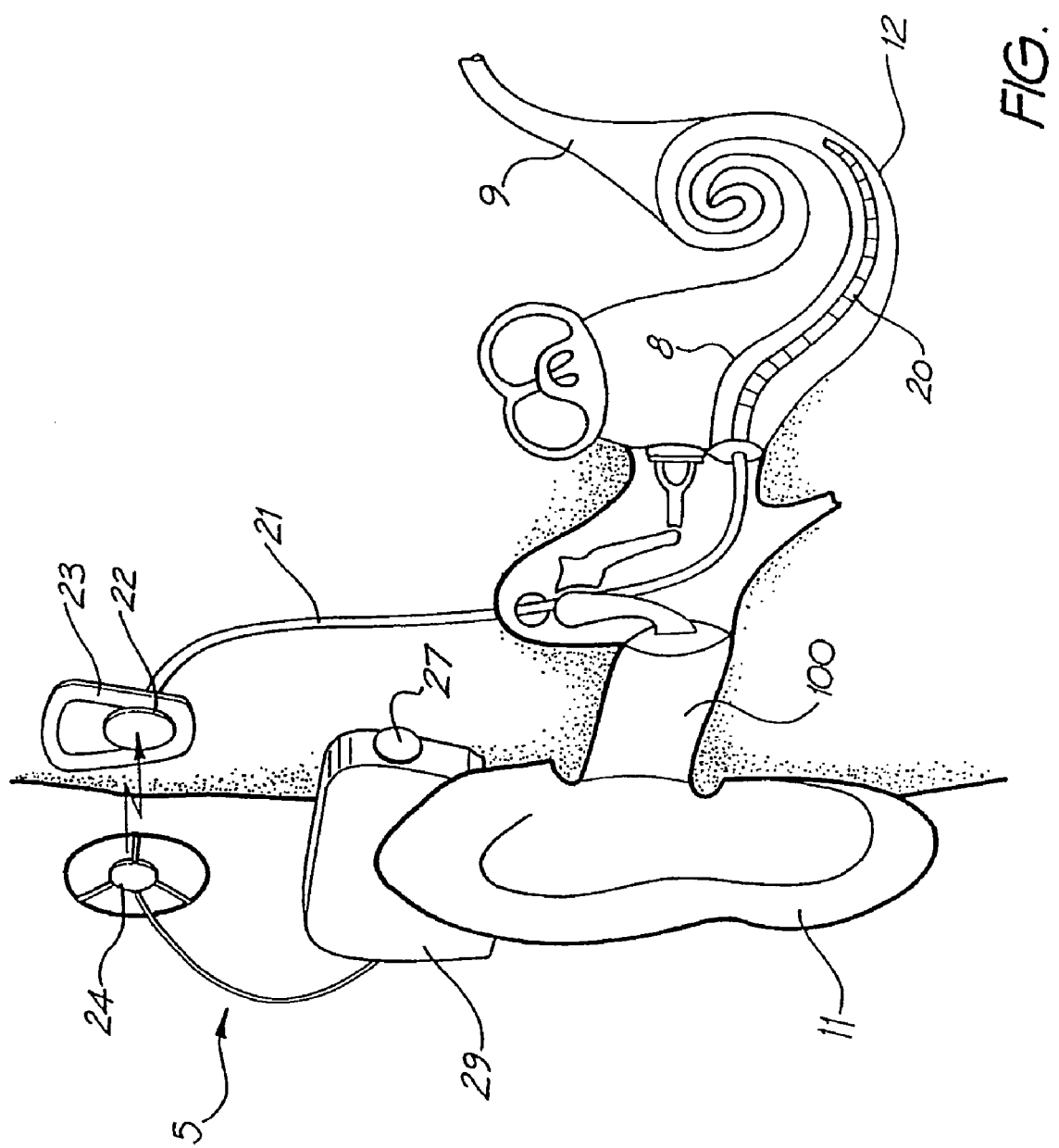
FIG. 1 is a pictorial representation of a prior art cochlear implant system.

While the present invention is not directed solely to a cochlear implant, it is appropriate to briefly describe the construction of one type of known cochlear implant system with reference to FIG. 1.

Known cochlear implants typically consist of two main components, an external component including a speech processor 29, and an internal component including an implanted receiver and stimulator unit 22. The external component includes a microphone 27. The speech processor 29 is, in this illustration, constructed and arranged so that it can fit behind the outer ear 11. Alternative versions may be worn on the body. Attached to the speech processor 29 is a transmitter coil 24 that transmits electrical signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 and the nerve cells within the cochlea 12 thereby stimulating the auditory nerve 9. The operation of such a device is described, for example, in U.S. Pat. No. 4,532,930.

As depicted diagrammatically in FIG. 1, the cochlear implant electrode array 20 has traditionally been inserted into the initial portion of the scala tympani of the cochlea 12 up to about a full turn within the cochlea.

Figure 2:
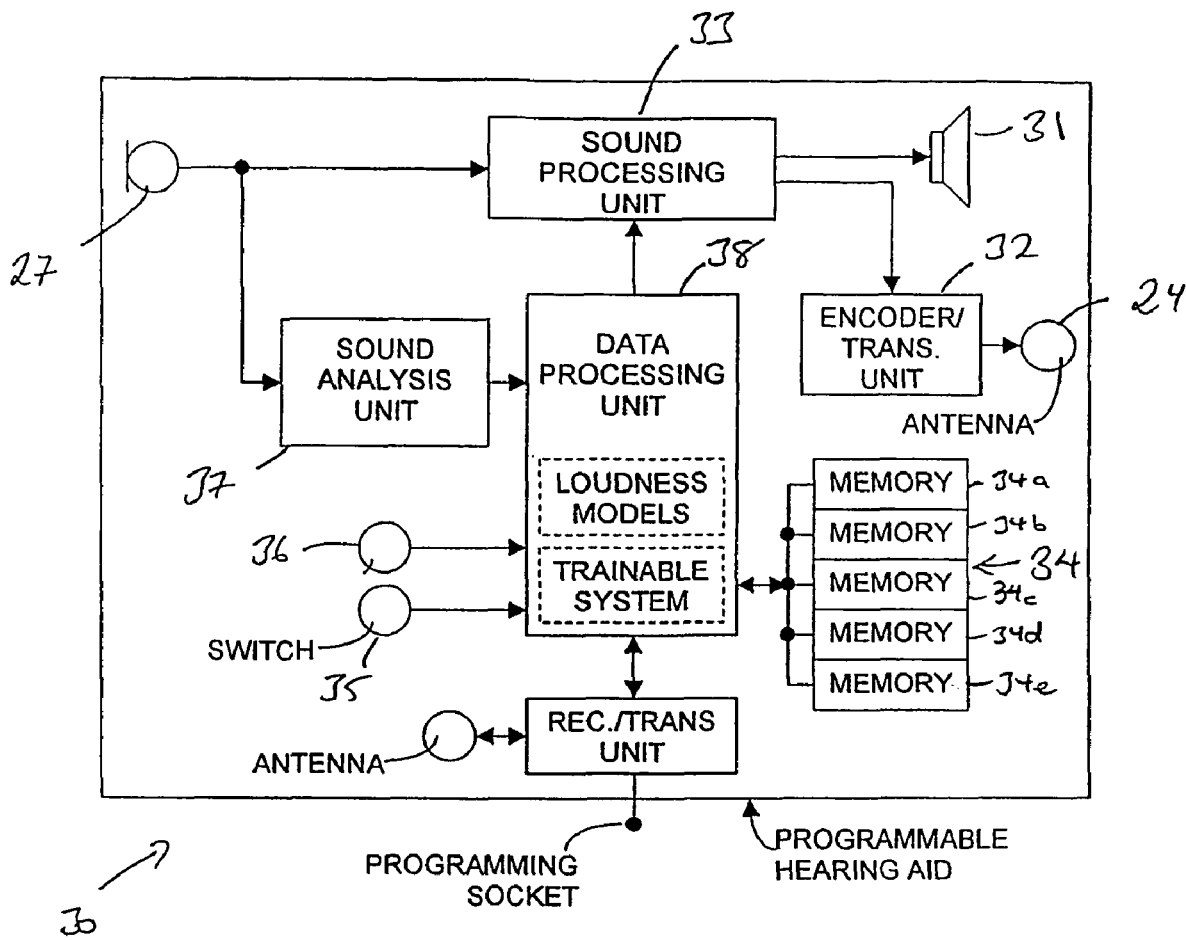
FIG. 2 is a block diagram of one embodiment of an auditory prosthesis according to the present invention.

A block diagram depicting one embodiment of an auditory prosthesis according to the present invention is depicted generally as 30 in FIG. 2. The block diagram depicts features of both a cochlear implant and a hearing aid. Despite this, it will be appreciated that the diagram is representative only and that a prosthesis according to the present invention may not necessarily act as both a cochlear implant and hearing aid.

The auditory prosthesis 30 comprises a microphone 27 which receives sound and produces a microphone signal corresponding to the received sound and an output device that provides audio signals in a form receivable by a user of the prosthesis 30. As can be seen, the output device can comprise an earphone 31 in the case where the prosthesis 30 is a hearing aid. Where the prosthesis 30 is a cochlear implant, the output device comprises an encoder/transmitter unit 32 that outputs encoded data signals to the external transmitter coil 24.

The prosthesis 30 further has a sound processing unit 33 that is operable to receive the microphone signal provided by the microphone 27 and produce an output signal in a form suitable to operate either the earphone 31 or the encoder/transmitter unit 32.

The nature and function of the sound processor 33 will depend on whether the prosthesis 30 is a cochlear implant or a hearing aid. In the case of a hearing aid, the sound processor 33 includes at least an amplifier whereas in the case of cochlear implant the sound processor 33 will include an amplifier and a speech processor that uses a coding strategy to extract speech from the sounds detected by the microphone 27. In the depicted embodiment, the speech processor of the cochlear implant can perform an audio spectral analysis of the acoustic signals and output channel amplitude levels. The sound processor can also sort the outputs in order of magnitude, or flag the spectral maxima as used in the SPEAK strategy developed by Cochlear Ltd. Other coding strategies could be employed.

In this invention, the sound processor 33 comprises at least one variable processing factor, such as amplification, which in a first mode of operation is adjustable to a setting in which the output signal of the sound processor 33 is optimised for the preference of the user in at least one acoustic environment. For example, the amplification characteristics of the amplifier can be adjusted by a user of the prosthesis 30 to suit the surrounding background noise in a particular environment.

The prosthesis 30 further comprises a data memory means 34 for storing at least data indicative of the setting selected by the user and optionally data sets representative of the characteristics of the acoustic environment at the time the setting adjustment and selection is made.

The sound processor 33 when operable in a first mode recalculates the trainable coefficients associated with a corresponding variable processing factor after each adjustment by the user.

The sound processor 33 can be adapted to offer two or more possible optimal settings for selection by the user. One of these settings may be the one automatically calculated by the processor and the other may be a systematic departure therefrom. In this case, the user is preferably able to compare the operation of the prosthesis when operating in a particular acoustic environment when operating with each setting and then select from these the setting that is best for that particular environment. The setting that is selected by the user can then be stored in the data memory means 34 optionally with data indicative of the particular acoustic environment. This process can be repeatable so as to allow the data processing unit 38 to gather the preferences and to monitor whether the user's preference for a particular environment changes with time or usage. In this way, the user effectively selects or votes for the best setting each time.

In this embodiment, the user can alternate between settings by operating a control means 36 which can be a toggle switch or a set of pushbuttons for example, and select a setting by operating an indicator means which is represented by switch 35 in FIG. 2. The switch 35 and control means 36 can be mounted on the housing of the prosthesis 30, or while not depicted, the switch and control means could be mounted on a remote unit.

The processing operation of the sound processor 33 can be operable in another manner or mode, in which its operation is adjustable by the user. Rather than offering a selection of possible optimal settings for selection by the user, in this arrangement, the user is able to adjust a control means 36 that allows the user to alter the processing operation of the sound processor unit 33. Once the user has adjusted the control means 36 to what is considered by the user an optimal setting for a particular acoustic environment, the user can operate the switch 35, leading to storage of that setting and optionally data indicative of the particular acoustic environment in the data memory means 34. Actuation of the switch 35 is taken by the sound processor unit 33 as indicating that the particular setting of the control means 36 at that time is considered optimal by the user for the particular acoustic environment in which the user finds themself.

The control means 36 can comprise a rotary wheel control that may be mounted on the housing of the prosthesis 30. The switch 35 can also be mounted on the housing of the prosthesis 30. While not depicted, the switch and controller could be mounted on a remote unit.

The settings selected by the user as being optimal to that user for a plurality of acoustic environments are stored in the data memory means 34 optionally with data indicative of those particular acoustic environments. The sound processor 33 continuously operates in the second mode, and can simultaneously be operable in the first mode for a defined period of time or can be considered as operating in that mode every time the user adjusts the control means 36 and selects what is considered a new optimal setting for that particular environment. The training period can be as long as the user wishes or optionally, the prosthesis 30 can signal to the user when the training period is complete. In this case, the prosthesis 30 can be adapted to indicate the training period is complete once there has been a particular pre-defined number of instances in which the user has been unable to select a setting that is substantially different from the setting already estimated by the prosthesis to be optimal.

The prosthesis 30 further comprises a sound analysis module 37. The sound analysis module 37 receives input signals from the microphone 27 and monitors the acoustic environment of the prosthesis user. The sound analysis module provides output(s) representative of the type of the acoustic environment being monitored at that time. In the depicted embodiment, the data memory means 34 comprises five data memory locations. In this embodiment, the first data memory means 34*a* contains the audiometric data of the prosthesis user and/or individual data for one or more loudness models used by the prosthesis 30. The second data memory location 34*b* contains characteristic data about the hearing prosthesis 30. The third data memory location 34*c* comprises one or more equations used to predict the optimal processing operation of the sound processor unit 33 for an individual user in different acoustic environments. The fourth data memory location 34*d* stores the optimal sound processing data as selected by the user. The acoustic environment data that corresponds to the optimal sound processing data stored in the fourth data memory location is optionally stored in the fifth data memory location 34*e*.

In the depicted embodiment, the fourth data memory location 34*d* stores a predefined maximum number of 400 sets of optimal sound processing data. Other maximum numbers can, however, be envisaged. The depicted embodiment uses a data processing unit 38, that is described in more detail below. The unit 38 does not utilise all stored data sets but only a predefined number of most recently logged data sets. In this case, the data processing unit 38 only utilises the last 256 data sets when calculating the optimal equation coefficients. Once the memory location is full, new data sets are stored in the memory location by overwriting the oldest data set in the memory location. This first in first out storage system ensures only the most recently logged data is ever stored in the prosthesis 30 at any one time. In another embodiment, older data cannot be overwritten such that once the memory location is full no further data sets can be logged by the prosthesis. In another embodiment, rules are used to determine the old data that is overwritten by the newest data set, based on the worth of each old data set according to predetermined criteria.

As indicated above, the prosthesis further comprises a data processing unit 38. The data processing unit 38 receives the output of the sound analysis module 37. Based on the output of the sound analysis module 37, the data processing unit 38 may be adapted to calculate the loudness of sounds present at the microphone 27. In the depicted embodiment, the data processing unit 38 may calculate the loudness of the sounds as they would appear to a person with normal hearing and/or to a person with a degree of hearing impairment. The data processing unit 38 can be adapted to calculate other acoustic and psychoacoustic measures of the sounds present at the microphone 27. The data processing unit 38 can use the measures of the acoustic conditions as inputs to the one or more equations stored in the third data memory location 34*c* which estimate the optimal sound processing operation of the sound processor 33 for the user in the acoustic environments determined by the sound analysis module 37.

The data processing unit 38 further uses the hearing prosthesis characteristic data stored in the second data memory location 34b and the optimal sound processor data generated by the equations to automatically and continuously determine the appropriate setting of the sound processor 33 to provide the optimal output signal for the user in the current acoustic environment being experienced by the user.

As described, the sound processor 33 includes an amplifier means and a control means 36. At all times the data processing unit 38 operates in the second mode, where it automatically calculates the operation of the sound processor 33 that is most likely to provide the optimal amplification characteristics in any environment, as represented by the output of sound analysis unit 37. The prosthesis can also simultaneously operate in the first mode, where operation of the amplifier means is also adjustable by the user varying control 36 to allow the user to optimise the amplification characteristics in the current acoustic environment.

Where the prosthesis 30 is used in any environment, including an environment never previously experienced by the user, the desired gain of the amplifier is calculated through use of an equation having a pre-defined form. In this embodiment, the equation is:

$$G_i = a_i + b_i * \max(L_i, c_i) + d_i * (SNR_i - SNR_{av}) \quad (1)$$

where i=the band number;
$G_i$=gain for band i;
$a_i$=trainable coefficient for band i;
$b_i$=trainable coefficient for band i;
$c_i$=trainable coefficient for band i;
$d_i$=trainable coefficient for band i;
$L_i$=sound pressure level at the microphone in band i;
$SNR_i$=signal to noise ratio in band i; and
$SNR_{av}$=average SNR in all bands.

For each vote, the following training data is stored for each band i:
the sound pressure level or SPL, $L_i$, in dB SPL;
the signal-to-noise ratio in band i minus the average for all bands, that is $SNR_i - SNR_{av}$, in dB; and
the preferred gain $G_i$ also in dB.

Each of the above values are calculated based on the signal at the microphone 27 for a period of time that precedes the actual vote. The values may be calculated based on the signal at the microphone 27 for a time preceding the vote and/or for a time after the vote has been cast. The stored Li is the average or RMS value of the SPL over the predetermined period of time and the stored Gi is the average value of the gain over a predetermined period of time prior to the actuation of the voting button plus the user's preferred gain adjustment at the time of actuation of the voting button. The SNR in band i is currently calculated at the SPL at the microphone exceeded 10% of the time in band i minus the SPL at the microphone exceeded 90% of the time in band i over the predetermined period of time prior to the vote. This difference may be more accurately described as an estimate of the modulation depth of the signal. It is envisaged that a more accurate SNR or even speech-to-noise ratio estimation techniques may be employed.

The stored training data from many votes, for example up to 256, is used to form a set of simultaneous equations (1). The set of simultaneous equations is stored as a set of linear equations, however since coefficient $b_i$ and coefficient $c_i$ are potentially multiplied by each other, that is not linear, the simultaneous equations are initially linearised. In other words the value of $c_i$ is set to a predefined value, and the MAX [$L_i$, $c_i$] operation performed with this value of $c_i$ and the stored $L_i$ values in order to set the bracketed term, in other words the greater of $L_i$ and $c_i$ the result of which is $L'_i$. Subsequently the optimal values of $a_i$, $b_i$ and $d_i$ are calculated with a direct numerical method wherein the optimal coefficient values are the ones that give the least squared error between the stored $G_i$ values and $G_i$ values that are calculated with the corresponding $L'_i$ and stored $SNR_i - SNR_{av}$ values. This is repeated for at least four alternative values of $c_i$, for example 35, 45, 55 and 65 dB SPL, and the set of coefficients that gives the least squared error is selected as the optimal set and applied to the processing of the signal, unless the value of $b_i$ is outside the range of −1.0 to +1.0, or if less than fifty votes have occurred. Other versions may apply the trained coefficients after more or less than fifty votes.

The direct numerical method used is lower-upper (LU) decomposition and back substitution which is a variant of Gaussian elimination the set of simultaneous equations are stored as matrices in memory, Ax=b, where matrix A contains the stored acoustic environment data, x is a vector that contains the coefficients to be calculated (that is $a_i$, $b_i$ and $d_i$), and b is a vector that contains the stored $G_i$ values. The LU decomposition method operates on these matrices and solves vector x. Other variants of Gaussian elimination or other direct numerical methods can be used in other applications.

As an example, the training data from four votes may result in the set of simultaneous equations as follows:

$$25 = a_i + (b_i * 35) + (d_i * 0)$$

$$20 = a_i + (b_i * 45) + (d_i * 0)$$

$$15 = a_i + (b_i * 55) + (d_i * 0)$$

$$10 = a_i + (b_i * 65) + (d_i * 0)$$

In this case, the trained coefficients would be $a_i$=42.5, $b_i$=−0.5, $c_i$=35 and $d_i$=0.0.

This set of coefficients would give 0 dB error. In practical situations, there may be more variability in people's amplification preferences, or scatter in the training data. Thus the preferred, user adjusted, $G_i$ values on the left of the equal signs in the above equations would not go up so uniformly in even steps, and the trained coefficient values would be different.

Other forms of the equation with other acoustic or psychoacoustic parameters, such as higher-order moments of the spectrum of the signal and variations of these moments with time, or other statistical parameters or estimates of the acoustic signal or combinations of these parameters, and optionally with other additional coefficients, can calculate the gain or processing factors other than gain, such as the speed at which the prosthesis reacts to change in the acoustic environment, the choice of the equations used will depend upon the particular application desired, with such applications falling within the scope of the present invention.

In the above embodiment, trainable coefficients include a, b, c and d, which as a result leads to the amplifier gain G being a variable processing factor.

More than one processing factor of the sound processor 33 can be automatically calculated using equations similar to equation 1, and then further adjusted by the user using the control means 36 or multiple control means. In this embodiment, the control means 36 can allow the user to adjust one or more of the following operations of the sound processor 33:

(i) the volume of the output signal;

(ii) the gain of the output signal at particular frequencies relative to other frequencies, for example the mid frequency gain can be boosted or attenuated with respect to the low or high band frequencies of the output signal; and (iii) a slope control where the low and high frequency band gains are adjusted in opposing directions while the mid band gain is unchanged.

The user can select which setting of the control means 36 is the optimal one for the particular acoustic environment that they are in by actuating the switch 35. Each time the switch 35 is actuated, the gain in each frequency band is logged along with a data set indicative of the acoustic environment detected by the microphone 27. This data can be used with previous sets of data by the data processing unit 38 to calculate the gain equation coefficients that enable the equations to best predict the preferences of the user from the logged training data in each band. Because the data processing unit 38 has access to the preferred amplification characteristics and the acoustic environments in which they were preferred, the data processing unit 38 can calculate general relationships between the amplification characteristics and the measured aspects of the acoustic environment. The automatically calculated amplification characteristics can thus vary in a complex but defined manner as the acoustic environment changes. For example, in the current embodiment, gain at each frequency varies with the overall input level and the signal-to-noise ratio at said frequency relative to the signal-to-noise ratio at other frequencies.

The depicted data processing unit 38 does not calculate optimal gain equation coefficients until a predetermined number of selections have been made by the user. In the depicted embodiment, the prosthesis 30 is adapted to not calculate optimal gain equation coefficients until at least fifty selections have been made by the user. In this case, where the predetermined number of selections have not been made, the sound processor 33 will preferably output a signal calculated on the basis of the initial, pre-defined values of trainable coefficients. These initial, pre-defined values are calculated for each user by conventional methods of prescribing prosthesis operation, or by an empirical, trial and error adjustment process. Once the predetermined number of selections have been made, the data processing unit 38 re-calculates the trainable coefficients immediately after every occasion on which the user operates the switch 35 to indicate that the control 36 is in the optimal position. In another embodiment, the data processing unit 38 does not wait until a predetermined number of selections have been made by the user to re-calculate the trainable coefficients, but does not apply these coefficients until the equations can accurately predict the preferences of the aid user with the trained coefficients, and/or the user has made selections in a preferred minimum range of acoustic environments.

In an alternative embodiment, a recursive-averaging equation is used to determine optimal (or trained) values for one or more coefficients.

For example, if the coefficient is the gain below the compression threshold (CT), then the optimal, trained setting can be determined using the equation:

$$g(n)=g(n-1)+w^*y^*\Delta G \qquad (2)$$

where n is the vote number g(n) is the trained gain below the CT after vote n w is a weighting factor ΔG is the adjustment made by the user to the variable processing factor, gain.

y=[90−L]/[90−CT] (calculated y set to within bounds: 0.0≦y≦1.0)

Similarly, if the coefficient is the compression ratio (CR), then the optimal, trained setting can be determined using the equation:

$$1/CR(n)=1/CR(n-1)+[w^*\Delta G^*(1-2y)]/[90-CT] \qquad (3)$$

where CR(n) is the trained CR after vote n

Similarly, if the coefficient is the compression ratio (CR), then the optimal, trained setting can be determined using the equation:

$$1/CR(n)=1/CR(n-1)+[w^*\Delta G^*(1-2y)]/[90-CT] \qquad (3)$$

where CR(n) is the trained CR after vote n

The trained values of the coefficients, as calculated with the recursive-averaging equations above, are then converted into coefficients of the following gain equation:

$$G=a+b^*MAX[L,c] \qquad (4)$$

In this example, c=CT, b=[1/CR(n)]−1, and a=g(n)−[b*c].

The aid user adjusts the output of the aid to his/her preference (in effect the aid user is adjusting the applied gain). After voting, the aid uses this output adjustment to calculate the trained compression ratio and gain below the compression threshold with the above recursive-averaging equations.

Therefore, a single output (or gain) adjustment by the aid user has been used to train two coefficients—the CR(n) and the gain below the CT, g(n). The CR(n) and g(n) values are used by the aid to continuously and automatically calculate the gain that is applied by the aid, G, with Eq. 4.

Note that Eq. 4 is very similar to the gain equation that is trained in the simultaneous equations method (a=g(n)−[b*c], b=[1/CR(n)]−1, and c=CT). Therefore, Eqs. 2 and 3 replace the simultaneous equations used in the earlier embodiment, and do not require the storage of a finite number of sets of preferred gain and corresponding acoustic environment data in the aid's memory.

The above can be repeated for i frequency channels. For example, there may be three frequency channels (low, mid, high) and the aid user may adjust the aid's output in each of these channels. The output adjustment for each channel would then be used to calculate the trained values of $CR(n)_i$ and $g(n)_i$ for each channel, and then $a_i$ and $b_i$ for each channel. The aid would then automatically calculate the applied gain, Gi, for each of the i channels many times per second for the current value of the input level, Li.

Figure 6:
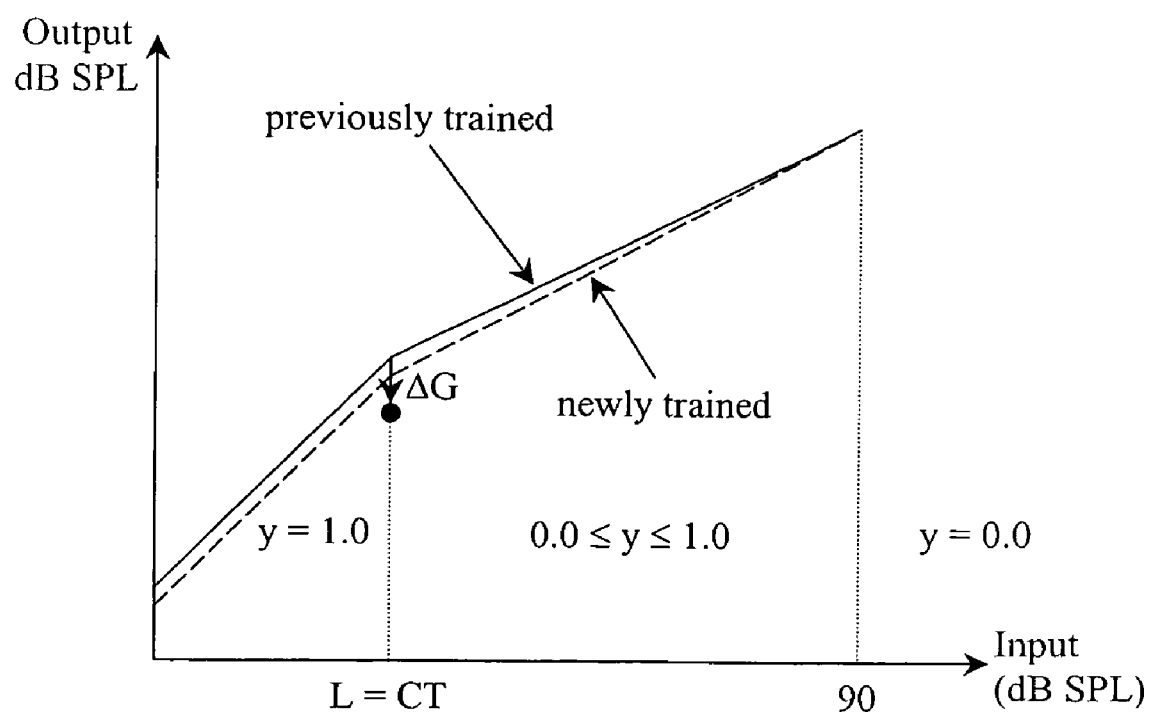
FIG. 6 is a graph showing a relationship between input and output sound pressure levels at various stages of the training process according to one embodiment of the present invention.

Referring to FIG. 6, the dot shows the preferred output level that was voted for by the aid user for the input level, L, that existed at the time. The solid line shows the input-output function before the vote, and ΔG is the gain adjustment that was voted for by the aid user. The dashed line shows the newly trained input-output function that may exist after this vote using the above recursive-averaging equations.

It will be appreciated that direct user adjustments can be made of the aid's settings (to his/her preference) and used to calculate an optimal set of coefficients with some sort of algorithm. The training algorithms can also be used to calculate the coefficients of other (i.e. non-gain) equations, as well as the values of variable processing factors that are not calculated with an equation, such as a global volume adjustment or the T level for an electrode of a cochlear implant.

In an alternative embodiment, the data processing unit 38 does not use the equations stored in the third data memory location 34c to determine the optimal variable processing factors for different environments. The optimally adjusted variable processing factors are stored in the fourth data memory location 34d at locations determined by the corresponding acoustic environment data supplied by the sound analysis means 37. Prior to the commencement of operation in the first mode, the fourth data memory locations 34d are loaded with processing factors that are derived from empirical observations or prescriptive procedures for the corresponding acoustic environment parameter values. When operating in the first mode the optimally adjusted processing factor(s) are stored in the fourth data memory 34d at locations determined by the acoustic environment data supplied by the sound analysis means 37. For example, the fourth data memory location 34d can store a multi-dimensional (or N-dimensional) look-up table or matrix, where each dimension is a different acoustic environment or psychoacoustic parameter, and the parameter values determine the location in the table, matrix, or memory location 34d where the preferred processing factor(s) is stored. Thus the matrix is indexed by rounded values of the N acoustic environment parameters (or optionally the estimated psychoacoustic parameters such as loudness). The optimally adjusted processing data may simply overwrite the prescribed data in the fourth data memory 34d, or may be combined with old data written to the same location using a mathematical and/or statistical procedure. When operating in the second mode, the acoustic environment and psychoacoustic parameter values supplied by the sound analysis means 37 are used to index the table or matrix or fourth data memory location 34d, and the value(s) stored at the indexed location are used to set the target value(s) of the corresponding processing factor(s) for the sound processing means 33. The processing factor(s) applied in the sound processing means 33 may slowly converge towards the target value(s) to avoid the possibility of undesirable acoustic effects associated with excessively rapid or instantaneous changes of the applied value(s). For memory locations that contain a prescribed value of a processing factor, the target value can be adjusted to represent the trend of user-adjusted values for environments located near the current environment in the memory location 34d. For this alternative embodiment there is no need for the fifth data memory location 34e and the equations stored in the third data memory 34c, and the variation of a processing factor with acoustic parameters supplied by the sound analysis means 37, or psychoacoustic parameters calculated by the data processing unit 38, is not restricted by the relationships that are predefined in the equations stored in the third data memory location 34c.

In one embodiment, the hearing prosthesis can be adapted to output audio signals to a single ear of the user. In another embodiment, the hearing prosthesis can be adapted to output audio signals to both ears of the user.

In a further embodiment, the trainable hearing prosthesis can be adapted to accept microphone signals from microphones mounted on each side of the head, and then to output signal to either or both ears.

Figure 3:
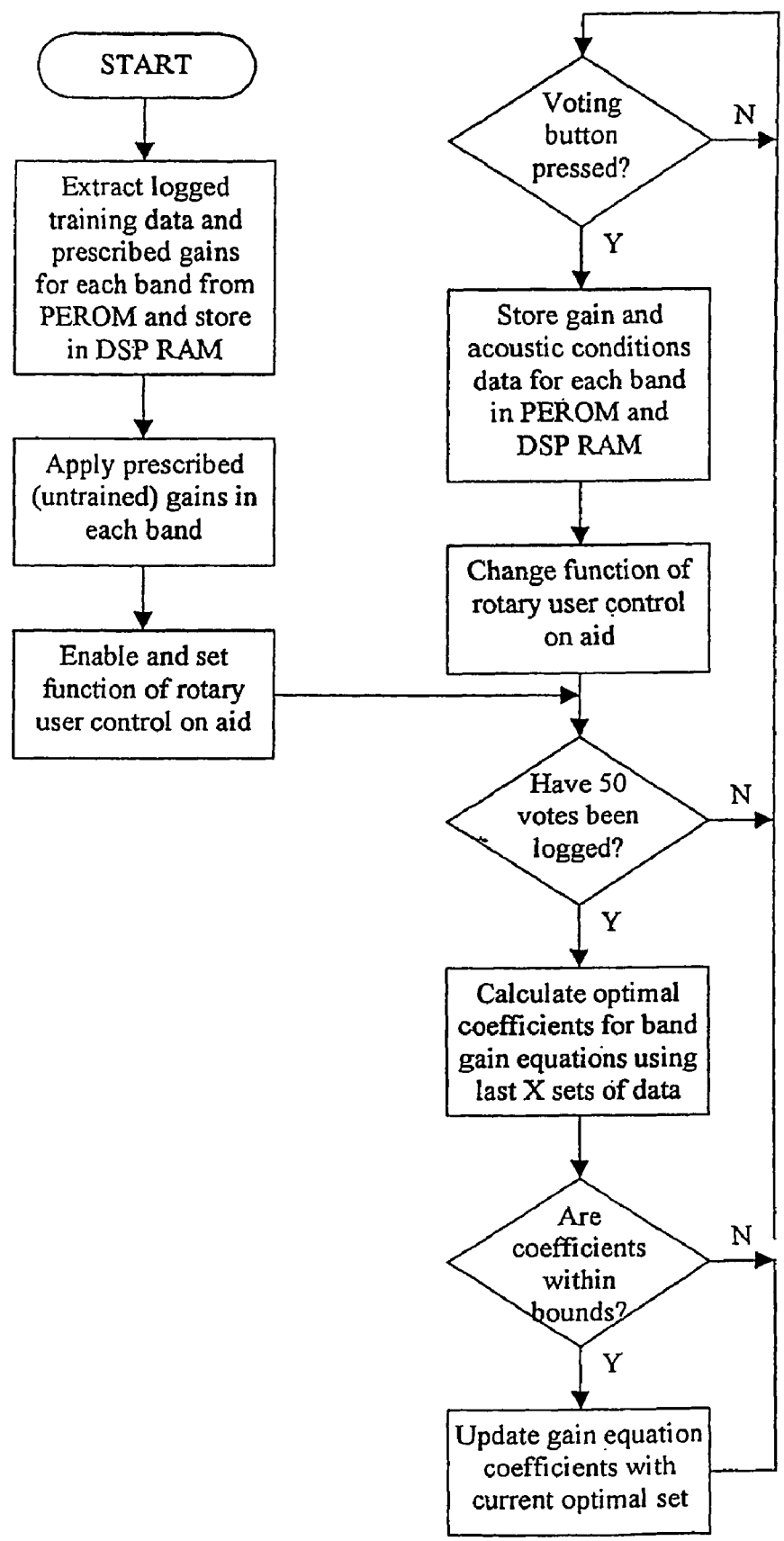
FIG. 3 is a flowchart setting one particular mode of operation of the prosthesis of FIG. 2.

FIG. 3 is a flowchart of the logic behind the operation of the data processing unit 38.

The Start of the flowchart is when the prosthesis 30 is turned on and power is supplied to the parts thereof including the sound processor 33 and data processing unit 38. The end point of the flowchart is when the user turns the prosthesis 30 off or if the battery for the power source goes flat. While not depicted, it is possible that another end point could be defined as when a certain number of votes are reached, or if the user stops training the prosthesis 30 for a predetermined period of time, or if the prosthesis 30 determines from the user adjustments of the control means 36 that it is sufficiently well-trained. Still further, an audiologist or other third party could disable further training of the prosthesis when the user is satisfied with the performance of the prosthesis 30 in a range of different acoustic environments. However, it is desirable that the user can train the prosthesis at any time, so that training does not need to be re-enabled if the user encounters a new environment or if the hearing loss profile of the user changes over time or with slow acclimatisation to the prosthesis.

Figure 4:
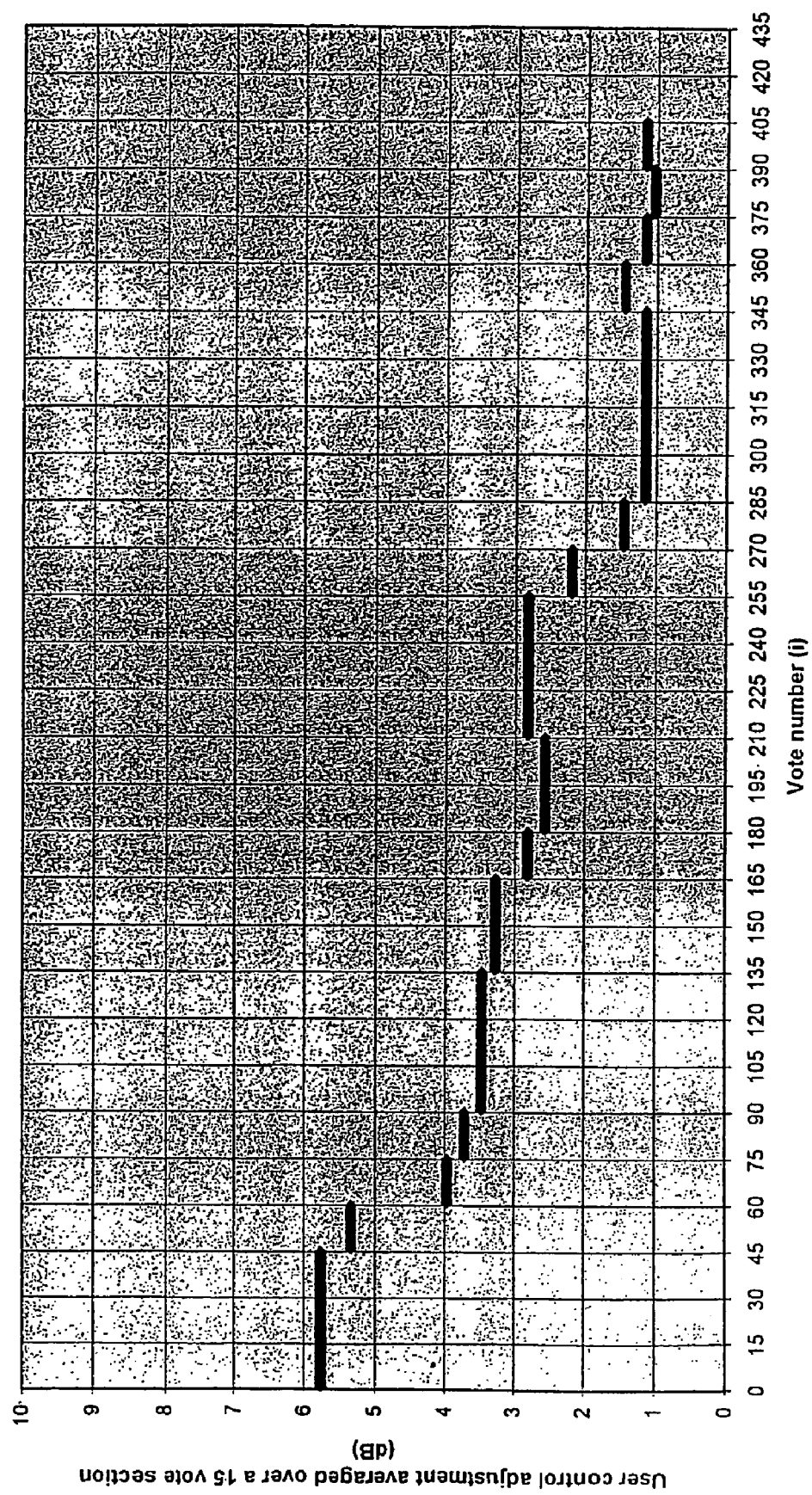
FIG. 4 is a graph depicting results of experiments performed on a prototype prosthesis according to one embodiment of the present invention.

FIG. 4 is a graph of the results of preliminary experiments performed on a prototype prosthesis according to the present invention. In the experiments, the goal was to train the prosthesis to produce a greater gain than provided by the prosthesis prior to the training in all frequency bands for any input sound. FIG. 4 indicates how the necessity to adjust the control 36 (RMS control adjustment in dB) following groups of 15 votes to get the desired output decreased due to the "training" ability of the prosthesis.

Figure 5:
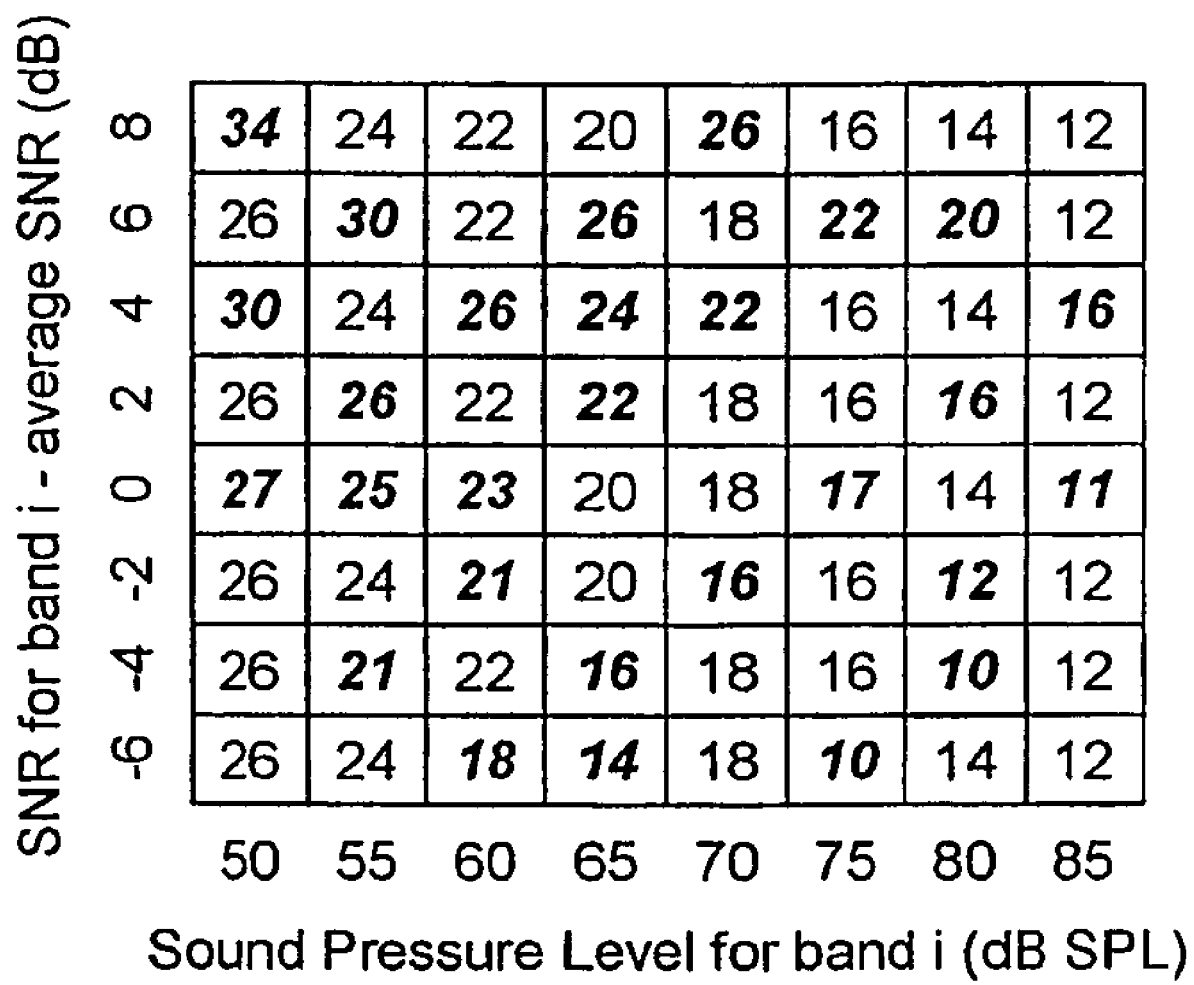
FIG. 5 is a diagram representing the storage of processing factor values in a two-dimensional memory space.

FIG. 5 is an illustration of the matrix previously referred to using acoustic parameters of equation 1.

FIG. 5 is a diagram representing the storage of processing factor values in a two-dimensional memory space that is indexed by the values of two acoustic parameters, the sound pressure level for band i and the signal-to-noise ratio for band i relative to the average for all bands, although this does not exclude the use of a greater number of dimensions from the scope of this invention, and the values shown are illustrative only. The numbers in the memory locations represent gain values, where gain is a variable processing factor. The stored values are prescribed values, except the bold italic values which represent data that differs from the initial prescribed data due to the storage of user-preferred setting data as a result of training by the user.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An auditory prosthesis for rehabilitating the hearing of a user, comprising:
    a microphone configured to receive sound and to produce a microphone signal corresponding to the received sound; and
    a sound processor configured to process the microphone signal using a set of variable processing factors, each having a value, to produce an output signal;
    wherein the prosthesis is configured to provide the user with the ability to individually adjust the value of at least one of the variable processing factors for a first particular acoustic environment; and
    wherein the prosthesis is further configured to automatically make subsequent adjustments to the value of the at least one variable processing factor for a second acoustic environment based on adjustments of the value of the at least one variable processing factor by the user.

2. The prosthesis according to claim 1, further comprising:
    data memory for storing the adjusted value of at least one processing factor.

3. The prosthesis according to claim 2, wherein the data memory further stores data sets representative of the characteristics of the acoustic environment in which the at least one variable processing factor was adjusted by the user.

4. The prosthesis according to claim 3, wherein value of the one or more variable processing factors are automatically adjusted on the basis of the acoustic environments in which the at least one variable processing factor was adjusted.

5. The prosthesis according to claim 2, wherein the data memory comprises one or more data memory locations.

6. The prosthesis according to claim 5, wherein the data memory comprises five data memory locations, and wherein a first data memory location stores audiometric data of the user and/or individual data for one or more loudness models used by the prosthesis.

7. The prosthesis according to claim 6, wherein a second data memory location stores characteristic data of the prosthesis.

8. The prosthesis according to claim 6, wherein a third data memory location stores one or more equations used by the sound processor.

9. The prosthesis according to claim 6, wherein a fourth data memory location stores the value of the at least one variable processing factor adjusted by the user.

10. The prosthesis according to claim 9, wherein the fourth data memory location stores a predefined maximum number of adjusted values of the at least one variable processing factor.

11. The prosthesis according to claim 9, wherein the data stored in the fourth data memory location is indexed according to the corresponding acoustic environment data supplied by the sound analysis unit.

12. The prosthesis according to claim 6, wherein a fifth data memory location stores acoustic environment data corresponding to the value of the at least one variable processing factor stored in the fourth data memory location.

13. The prosthesis according to claim 5, wherein the value of the at least one adjusted variable processing factor is stored at the one or more locations as determined by corresponding acoustic environment data supplied by the sound analysis unit.

14. The prosthesis according to claim 13, wherein the adjusted at least one variable processing factor is in a multi-dimensional look-up table where each dimension is a different acoustic environment or psychoacoustic parameter.

15. The prosthesis according to claim 14, wherein the multi-dimensional look-up table is indexed by at least two parameters chosen from acoustic environment parameters or psychoacoustic parameters.

16. The prosthesis according to claim 15, wherein the parameters determine the location in the look-up table in which preferred variable processing factors are stored.

17. The prosthesis according to claim 5, wherein the at least one adjusted variable processing factor is stored at the one or more locations as calculated by a mathematical and/or statistical procedure.

18. The prosthesis according to claim 2, wherein the prosthesis is configured to provide the user with the ability to repeatedly adjust the value of the at least one variable processing factor.

19. The prosthesis according to claim 18, wherein the prosthesis is configured to use a predefined number of the most recent adjustments of the value of the at least one variable processing factor to automatically adjust the one or more variable processing factors.

20. The prosthesis according to claim 18, wherein each adjustment of the value of the at least one variable processing factor by the user is monitored by the sound processor.

21. The prosthesis according to claim 20, wherein the user operates a control means to adjust the value of the at least one variable processing factor.

22. The prosthesis according to claim 1, wherein the at least one variable processing factor comprses an amplifier gain.

23. The prosthesis according to claim 1, wherein the prosthesis is configured to provide the user with the ability to adjust the value of the at least one variable processing factor only during a defined training period.

24. The prosthesis according to claim 23, wherein the prosthesis is configured to automatically adjust the one or more variable processing factors only after the value of the at least one variable processing factor has been adjusted by the user a predefined number of instances.

25. The auditory prosthesis according to claim 24, wherein the predetermined number of adjustments is fifty.

26. The prosthesis according to claim 24, wherein until the predetermined number of selections has been made, the sound processor processes the microphone signal using an initial, predefined set of variable processing factors.

27. The prosthesis according to claim 26 wherein the initial predefined values are calculated for each user via an empirical, trial and error adjustment process.

28. The prosthesis according to claim 23, wherein the prosthesis signals to the user when the training period is complete.

29. The prosthesis according to claim 1, further comprising:
a sound analysis unit configured to receive input signals from the microphone, and to monitor the current acoustic environment in which the prosthesis is operating.

30. The prosthesis according to claim 29, wherein the sound analysis unit provides an output representative of the monitored acoustic environment.

31. The prosthesis according to claim 30, further comprising a data processing unit configured to receive the output of the sound analysis unit.

32. The prosthesis according to claim 31, wherein the data processing unit, based on the output from the sound analysis unit, calculates acoustic and/or psychoacoustic measures, such as loudness, of the sound received at the microphone.

33. The prosthesis according to claim 32, wherein the data processing unit is configured to calculate the loudness of the received sound in relation to the loudness of the sound to a person with normal hearing and/or to a person with a degree of hearing impairment.

34. The prosthesis according to claim 31, wherein the data processing unit is adapted to calculate the loudness of sounds present at the microphone based on the output from the sound analysis unit.

35. The prosthesis according to claim 1, wherein the prosthesis is configured to provide the user with the ability to adjust the value of more than one variable processing factor.

36. The prosthesis according to claim 35, wherein the prosthesis comprises a controller configured to individually adjust the value of a first variable processing factor of the variable processing factors; and wherein the prosthesis is further configured to modify the function of the controller so that, after modification, the controller is configured to individually adjust the value of a second variable processing factor of the variable processing factors.

37. The prosthesis according to claim 35, wherein the prosthesis comprises a controller configured to individually adjust the value of the at least one variable processing factor along a continuum or to discrete values along a continuum, and wherein the value of at least one other processing factor is adjusted in response to the adjustment of the at least one variable processing factor.

38. The prosthesis according to claim 35, wherein the prosthesis comprises a plurality of controllers each configured to individually adjust the value of a variable processing factor of the at least one variable processing factors.

39. The prosthesis according to claim 35, wherein the at least one variable processing factor comprises: a volume of the output signal; a gain of the output signal at particular frequencies relative to other frequencies; and a slope of a gain-frequency response wherein low and high frequency band gains are adjusted in opposing directions while a midband gain is unchanged.

40. The prosthesis according to claim 1, wherein the prosthesis is configured such that the one or more automatically adjusted processing factors converge towards target values.

41. The prosthesis according to claim 1, wherein the prosthesis is configured to further base the adjustment of the one or more variable processing factors on values of acoustic environment and/or psychoacoustic parameters that are known to correlate with different listening criteria.

42. The prosthesis according to claim 41, wherein the prosthesis automatically predicts the listening criterion or criteria from the presence of speech and/or music signals of interest detected by the prosthesis.

43. The prosthesis according to claim 41, wherein the user indicates the current listening criteria or criterion via an indicator.

44. The prosthesis of claim 1, wherein the prosthesis is configured to automatically make subsequent adjustments by calculating a value for the at least one variable processing factor based on a characteristic of a current acoustic environment and the prior adjustments of the value of the at least one variable processing factor by the user.

45. A method of rehabilitating the hearing of a user, comprising:
- converting a received sound to a microphone signal;
- processing the microphone signal at a speech processor to generate an output signal utilizing a set of variable processing factors;
- receiving from a user an adjustment of the individual value of at least one of the variable processing factors of the set for a first acoustic environment;
- automatically adjusting one or more of the values of the at least one variable processing factor for a second acoustic environment based on the received adjustments of the value of the at least one variable by the user.

46. A method of claim 45, wherein automatically adjusting one or more of the values of the at least one variable processing factor comprises:
- calculating a value for the at least one variable processing factor based on a characteristic of a current acoustic environment and the prior adjustments of the value of the at least one variable processing factor by the user.

\* \* \* \* \*